(12) United States Patent
Nanikashvili et al.

(10) Patent No.: US 7,996,187 B2
(45) Date of Patent: Aug. 9, 2011

(54) METHOD AND SYSTEM FOR HEALTH MONITORING

(75) Inventors: Reuven Nanikashvili, Ashdod (IL); Nir Geva, Nes Ziona (IL)

(73) Assignee: Card Guard Scientific Survival Ltd., Rehovot (IL)

( * ) Notice: Subject to any disclaimer, the term of this patent is extended or adjusted under 35 U.S.C. 154(b) by 347 days.

(21) Appl. No.: 11/968,224

(22) Filed: Jan. 2, 2008
(Under 37 CFR 1.47)

(65) Prior Publication Data
US 2011/0009711 A1    Jan. 13, 2011

Related U.S. Application Data

(63) Continuation-in-part of application No. 11/059,791, filed on Feb. 16, 2005, now Pat. No. 7,542,878.

(51) Int. Cl.
*G06F 19/00* (2011.01)
(52) U.S. Cl. .................................. 702/188; 600/300
(58) Field of Classification Search .................. 702/188, 702/182–185; 600/300
See application file for complete search history.

(56) References Cited

U.S. PATENT DOCUMENTS

| | | | |
|---|---|---|---|
| 3,776,228 A | 12/1973 | Semler | |
| 3,779,249 A | 12/1973 | Semler | |
| 4,364,397 A | 12/1982 | Citron et al. | |
| 4,531,527 A | 7/1985 | Reinhold | |
| 4,572,182 A | 2/1986 | Royse | |
| 4,583,553 A | 4/1986 | Shah et al. | |
| 4,622,979 A | 11/1986 | Katchis et al. | |
| 4,625,730 A | 12/1986 | Fountain et al. | |
| 4,803,625 A | 2/1989 | Fu et al. | |
| 4,889,131 A | 12/1989 | Salem et al. | |
| 4,920,489 A | 4/1990 | Hubelbank et al. | |
| 4,938,228 A | 7/1990 | Righter et al. | |
| 4,958,641 A | 9/1990 | Digby et al. | |
| 4,967,756 A | 11/1990 | Hewitt | |
| 4,977,899 A | 12/1990 | Digby et al. | |
| 5,012,814 A | 5/1991 | Mills et al. | |
| 5,058,597 A | 10/1991 | Onoda et al. | |
| 5,090,418 A | 2/1992 | Squires et al. | |
| 5,111,396 A | 5/1992 | Mills et al. | |

(Continued)

FOREIGN PATENT DOCUMENTS

EP    0957964 A1    11/1997

(Continued)

OTHER PUBLICATIONS

Braemar-eCardio's Initial Non-Infringement, Invalidity and Unenforceability; *Lifewatch v. Braemar* (IL) Civil Action No. 09-06001; filed Feb. 17, 2010.

(Continued)

*Primary Examiner* — Edward Raymond
(74) *Attorney, Agent, or Firm* — Reches Patents

(57) ABSTRACT

A personal health monitor, including: (a) a physiological data input device operative to gather physiological data; and (b) a multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity; wherein the physiological data input device controls a transmission of the physiological data to the multi-purpose personal data accessory.

19 Claims, 14 Drawing Sheets

U.S. PATENT DOCUMENTS

| | | |
|---|---|---|
| 5,128,552 A | 7/1992 | Fang et al. |
| 5,181,519 A | 1/1993 | Bible |
| 5,191,891 A | 3/1993 | Righter |
| 5,201,321 A | 4/1993 | Fulton |
| 5,205,295 A | 4/1993 | Del Mar et al. |
| 5,226,424 A | 7/1993 | Bible |
| 5,226,425 A | 7/1993 | Righter |
| 5,238,001 A | 8/1993 | Gallant et al. |
| D341,659 S | 11/1993 | Homayoun et al. |
| 5,289,824 A | 3/1994 | Mills et al. |
| 5,304,186 A | 4/1994 | Semler et al. |
| 5,313,953 A | 5/1994 | Yomtov et al. |
| 5,317,269 A | 5/1994 | Mills et al. |
| 5,333,616 A | 8/1994 | Mills et al. |
| 5,339,824 A | 8/1994 | Engira |
| 5,343,869 A | 9/1994 | Pross et al. |
| 5,343,870 A | 9/1994 | Gallant et al. |
| 5,348,008 A | 9/1994 | Bornn et al. |
| 5,351,695 A | 10/1994 | Mills et al. |
| 5,365,935 A | 11/1994 | Righter et al. |
| 5,417,222 A | 5/1995 | Dempsey et al. |
| 5,467,773 A | 11/1995 | Bergelson et al. |
| 5,518,001 A | 5/1996 | Snell |
| 5,522,396 A | 6/1996 | Langer et al. |
| D372,785 S | 8/1996 | Sabri et al. |
| 5,544,661 A | 8/1996 | Davis et al. |
| 5,581,369 A | 12/1996 | Righter et al. |
| D377,983 S | 2/1997 | Sabri et al. |
| 5,613,495 A | 3/1997 | Mills et al. |
| 5,652,570 A | 7/1997 | Lepkofker |
| 5,678,562 A | 10/1997 | Sellers |
| 5,701,894 A | 12/1997 | Cherry et al. |
| 5,704,364 A | 1/1998 | Saltzstein et al. |
| 5,724,025 A | 3/1998 | Tavori |
| 5,730,143 A | 3/1998 | Schwarzberg |
| 5,772,586 A | 6/1998 | Heinonen |
| 5,807,336 A | 9/1998 | Russo et al. |
| 5,827,179 A | 10/1998 | Lichter et al. |
| 5,840,020 A | 11/1998 | Heinonen et al. |
| 5,873,369 A | 2/1999 | Laniado et al. |
| 5,877,675 A | 3/1999 | Rebstrock et al. |
| 5,885,245 A | 3/1999 | Lynch et al. |
| 5,895,371 A | 4/1999 | Levitas et al. |
| 5,929,761 A | 7/1999 | Van der Laan et al. |
| 5,941,829 A | 8/1999 | Saltzstein et al. |
| D414,870 S | 10/1999 | Saltzstein et al. |
| 6,053,887 A | 4/2000 | Levitas et al. |
| D427,315 S | 6/2000 | Saltzstein et al. |
| 6,072,396 A | 6/2000 | Gaukel et al. |
| 6,083,248 A | 7/2000 | Thompson |
| 6,084,510 A | 7/2000 | Lemelson et al. |
| 6,100,806 A | 8/2000 | Gaukel et al. |
| 6,135,949 A | 10/2000 | Russo et al. |
| 6,159,147 A | 12/2000 | Lichter et al. |
| 6,173,198 B1 | 1/2001 | Schulze et al. |
| 6,198,394 B1 | 3/2001 | Jacobsen et al. |
| 6,231,560 B1 | 5/2001 | Bui et al. |
| 6,364,834 B1 | 4/2002 | Reuss et al. |
| 6,366,871 B1 | 4/2002 | Geva |
| 6,398,727 B1 | 6/2002 | Bui et al. |
| 6,478,736 B1 | 11/2002 | Mault |
| 6,513,532 B2 | 2/2003 | Mault |
| 6,549,756 B1 | 4/2003 | Engstrom |
| 6,579,231 B1 | 6/2003 | Phipps |
| 6,595,929 B2 | 7/2003 | Stivoric et al. |
| 6,616,613 B1 | 9/2003 | Goodman |
| 6,790,178 B1 | 9/2004 | Mault et al. |
| 6,871,089 B2 | 3/2005 | Korzinov et al. |
| 7,009,511 B2 | 3/2006 | Mazar et al. |
| 7,108,659 B2 | 9/2006 | Ross et al. |
| 7,188,151 B2 | 3/2007 | Kumar et al. |
| 7,222,054 B2 | 5/2007 | Geva |
| 7,299,159 B2 | 11/2007 | Nanikashvili |
| 7,542,878 B2 | 6/2009 | Nanikashvili |
| 7,596,405 B2 | 9/2009 | Kurzweil et al. |
| 2001/0027384 A1 | 10/2001 | Schulze |
| 2002/0032386 A1 | 3/2002 | Sackner et al. |
| 2002/0032387 A1 | 3/2002 | Geva et al. |
| 2003/0028442 A1 | 2/2003 | Wagstaff et al. |
| 2003/0107487 A1 | 6/2003 | Korman et al. |
| 2003/0149344 A1 | 8/2003 | Nizan |
| 2004/0059205 A1 | 3/2004 | Carlson et al. |
| 2004/0143403 A1* | 7/2004 | Brandon et al. ............ 702/19 |
| 2004/0266480 A1 | 12/2004 | Hjelt et al. |

FOREIGN PATENT DOCUMENTS

| | | |
|---|---|---|
| EP | 1782229 | 8/2009 |
| GB | 2372114 A | 8/2002 |
| WO | WO 01/47597 | 7/2001 |
| WO | WO 02/080762 A1 | 10/2002 |
| WO | WO 2006/001005 A2 | 5/2006 |
| WO | WO2007/083315 | 7/2007 |

OTHER PUBLICATIONS

Braemar-eCardio's Exhibits C-O to Disclosure; *Lifewatch* v. *Braemar* (IL) Civil Action No. 09-06001; filed Feb. 17, 2010.

Mednet's Initial Non-infringement, Invalidity and Unenforceability: *Lifewatch* v. *Braemar* (IL) Civil Action No 09-06001; filed Feb. 17, 2010.

Mednet's Exhibit D—Initial invalidity Contentions; *Lifewatch* v. *Braemar* (IL) Civil Action No. 09-06001; filed Feb. 17, 2010.

LW's Responses to Braemar & eCardio's Initial Invalidity Contentions; *Lifewatch* v. *Braemar* (IL) Civil Action No. 09-06001; filed Mar. 3, 2010.

LW's Exhibits 1-13 to its Responses to Braemar & eCardio's Initial Invalidity Contentions; *Lifewatch* v. *Braemar* (IL) Action No. 09-06001; filed Mar. 3, 2010.

LW's Responses to Mednet's Initial Invalidity Contentions; *Lifewatch* v. *Braemar* (IL) Civil Action No. 09-06001; filed Mar. 3, 2010.

LW's Exhibits 10-20 to its Responses to Mednet's Initial Invalidity Contentions; *Lifewatch* v. *Braemar* (IL) Civil Action No. 09-06001; flied Mar. 3, 2010.

037.00—Defendants' Opposition to LifeWatch's Motion for PI; *Lifewatch* v. *Medicomp* (FL) 09-CV-01909 Orl-3IDAB; filed Dec. 16, 2009.

040.00—Declaration of Shatzer in Opp to Mtn for PI; *Lifewatch* v. *Medicomp* (FL) 09-CV-01909-Orl-31DAB; filed Dec. 16, 2009.

040.18—Exhibit 11; *Lifewatch* v. *Medicomp* (FL) 09-CV-01909-Orl-31DAB; filed Dec. 16, 2009.

040.20—Exhibit 13; *Lifewatch* v. *Medicomp* (FL) 09-CV-01909-Orl-31DAB; filed Dec. 16, 2009.

046.02—Shatzer Amended Exhibit 15; *Lifewatch* v. *Medicomp* (FL) 09-CV-01909-Orl-31DAB; filed Jan. 6, 2010.

040.24—Exhibit 17; *Lifewatch* v. *Medicomp* (FL) 09-CV-01909-Orl-31DAB; filed Dec. 16, 2009.

040.25—Exhibit 18; *Lifewatch* v. *Medicomp* (FL) 09-CV-01909-Orl-31DAB; filed Dec. 16, 2009.

040.26—Exhibit 19; *Lifewatch* v. *Medicomp* (FL) 09-CV-01909-Orl-31DAB; filed Dec. 16, 2009.

040.28—Exhibit 21; *Lifewatch* v. *Medicomp* (FL) 090-CV-01909-Orl-31DAB; filed Dec. 16, 2009.

040.34—Exhibit 27; *Lifewatch* v. *Medicomp* (FL) 09-CV-01909-Orl-31DAB; filed Dec. 16, 2009.

040.36—Exhibit 29; *Lifewatch* v. *Medicomp* (FL) 09-CV-01909-Orl-31DAB; filed Dec. 16, 2009.

053.00—Reply Brief Supporting Motion for Preliminary Injunction; *Lifewatch* v. *Medicomp* (FL) 09-CV-01909-Orl-31DAB; filed Jan. 15, 2010.

064.00—Medicomp's Demonstrative Presentation as Presented at 1.28.10 Evidentiary Hearing; *Lifewatch* v. *Medicomp* (FL) 09-CV-01909-Orl-31DAB; filed Jan. 28, 2010.

064.01—pp. 21-40; *Lifewatch* v. *Medicomp* (FL) 09-CV-01909-Orl-31DAB; filed Jan. 28, 2010.

064.02—pp. 41-60; *Lifewatch* v. *Medicomp* (FL) 09-CV-01909-Orl-31DAB; filed Jan. 28, 2010.

064.03—pp. 61-80; *Lifewatch* v. *Medicomp* (FL) 09-CV-01909-Orl-31DAB; filed Jan. 28, 2010.

064.04—pp. 81-100; *Lifewatch* v. *Medicomp* (FL) 09-CV-01909-Orl-31DAB; filed Jan. 28, 2010.

064.05—pp. 101-119; *Lifewatch* v. *Medicomp* (FL) 09-CV-01909-Orl-31DAB; filed Jan. 28, 12010.

068.00—Plaintiffs Demonstrative; *Lifewatch* v. *Medicomp* (FL) 09-CV-01909-Orl-31DAB; filed Jan. 28, 2010.

070.00—Defendants' Response to Plaintiffs' Proposal in Connection with PI & Scheduling; *Lifewatch* v. *Medicomp* (FL) 09-CV-01909-Orl-31DAB; filed Feb. 2, 2010.

071.00 Order Denying Motion for Preliminary Injunction; *Lifewatch* v. *Medicomp* (FL) 09-CV-01909-Orl-31DAB; filed Feb. 10, 2010.

081.00—Order granting in part [75] Mob to Stay; *Lifewatch* v. *Medicomp* (FL) 09-CV-01909-Orl-31DAB; filed Mar. 16, 2010.

WO 06/001005 A3 International Search Report, Internatianal Preliminary Report on Patentability and Written Opinion of the International Searching Authority mailed Jun. 29, 2006, for International Patent Application No. PCT/IL2005/000664.

Gomez, "A telemedicine distributed decision-Support System for Diabetes Management," IEEE, Oct. 29, 1992, pp. 1238-1239, USA.

Wiesspeiner & Wu, "Multichannel Ambulatory Monitoring of Circulation Related Biosignals," IEEE, Sep. 23, 1991, pp. 457-460, USA.

Author unknown, "ActiveECG Manual," date unknown, pp. 1-56, location published, unknown. (ActiveECG system may have been offered for sale at least since 2001).

Biosensor Corp., "Full Disclosure, Scanning and More!" (brochure for Uniday system), date unknown, printed in USA. (Uniday system may have been offered for sale at least as early as 1987).

Biosensor Corp., "Multiday Interactive Monitoring," (brochure for Multiday system), date unknown, printed in USA. (Multiday system may have been offered for sale at least as early as 1987).

Sony Corp., "Operating Instructions, Sony Clie Personal Entertainment Organizer PEG-NX70V, PEG NX60," 2002, pp. 1-100, location published unknown.

EP Patent Application No. 99906437.1, International Search Report dated Aug. 30, 1999.

EP Patent Application No. 99906437.1, Amendment & Substitute dated Nov. 11, 1999.

EP Patent Application No. 03743496.6, International Search Report dated Dec. 31, 2003.

EP Patent Application No. 03743496.6, Amendment dated Sep. 27, 2004.

EP Patent Application No. 03743496.6, Supplementary European Search Report dated Apr. 3, 2009.

EP Patent Application No. 03743496.6, Communication from Examining Division dated Oct. 14, 2009.

EP Patent Application No. 03743496.6, Reply to Communication from Examining Division dated Apr. 19, 2010.

EP Patent Application No. 05774734.7, International Search Report dated May 26, 2006.

EP Patent Application No. 05774734.7,International Preliminary Report on Patentability dated Mar. 12, 2007.

EP Patent Application No. 05774734.7, Supplementary European Search Report dated Aug. 27, 2009.

EP Patent Application No. 05774734.7, European Search Opinion dated Aug. 27, 2009.

EP Patent Application No. 05774734.7, Reply to Communication from Examining Division dated Apr. 21, 2010.

EP Patent Application No. 05754578.2, International Search Report dated Aug. 24, 2006.

EP Patent Application No. 05754578.2, International Preliminary Report on Patentability dated Jan. 15, 2007.

EP Patent Application No. 05754578.2, Supplementary European Search Report dated Feb. 18, 2009.

EP Patent Application No. 05754578.2, Communication from Examining Division dated Aug. 4, 2009.

EP Patent Application No. 05754578.2, Reply to Communication from Examining Division dated Feb. 4, 2010.

Gomez, "A Telemedicine Distributed Decision-Support System for Diabetes Management," IEEE, Oct. 9, 1992, pp. 1238-1239, USA.

Wiesspeiner & Wu, "Multichannel Ambulatory Monitoring of Circulation Related Biosignals," in Sep. 23, 1991, pp. 457-460, USA.

Author Unknown, "ActiveECG Manual," Date Unknown, pp. 1-56, Location Published Unknown. (ActiveECG system may have been offered for sale at least since 2001).

Biosensor Corp., "Full Disclosure, Scanning and More!" (brochure for Uniday system), Date Unknown, Printed in USA. (Uniday system may have been offered for sale at least as early as 1987).

Biosensor Corp., "Multiday Interactive Monitoring," (brochure for Multiday system) Date Unknown, Printed in USA. (Multiday system may have been offered for sale at least as early as 1987).

Sony, "Operating Instructions, Sony Clie Personal Entertainment Organizer PEG-NX70V, PEG NX60," 2002, pp. 1-100.

Braemar-eCardio's initial non-infringement, invalidity and unenforceability; *Lifewatch* v. *Braemar* (IL) Civil Action No. 09-06001; filed Feb. 17, 2010.

Braemar-eCardio's Exhibits P—R to Disclosure; *Lifewatch* v. *Braemar* (IL) Civil Action No. 09-06001; filed Feb. 17, 2010.

Mednet's Initial non-infringement, invalidity and unenforceability; *Lifewatch* v. *Braemar* (IL) Civil Action No. 09-06001; filed Feb. 17, 2010.

Exhibit C—Mednet's Initial Invalidity Contentions; *Lifewatch* v. *Braemar* (IL) Civil Action No. 09-06001; filed Feb. 17, 2010.

Braemar_and_eCardio_s_Amended_Joint_Disc_of_Init_Invalidity_Cont_Concerning_143_Patent; *Lifewatch* v. *Braemar* (IL) Civil Action No. 09-06001; filed Feb. 23, 2010.

LW's Responses to Braemar & eCardio's Initial lnvalidity Contentions; *Lifewatch* v. *Braemar* (IL) Civil Action No. 09-06001; filed Mar. 3, 2010.

LW's Exhibits 14-16 to its Responses to Braemar & eCardio's Initial Invalidity Contentions; *Lifewatch* v. *Braemar* (IL) Civil Action No. 09-06001; filed Mar. 3, 2010.

LW 's Exhibits 1-9 to its Responses to Mednet's Initial Invalidity Contentions; *Lifewatch* v. *Braemar* (IL) Civil Action No. 09-06001; filed Mar. 3, 2010.

Joint_Disclosure_of_Final_Invalidity_and_Unenforceability_Contentions; *Lifewatch* v. *Braemar* (IL) Civil Action No. 09-06001; filed Jun. 23, 2010.

Exhibits_to_Final_Invalidiity_and_Unenforceability_Contentions; *Lifewatch* v. *Braemar* (IL) Civil Action No. 09-06001; filed Jun. 23, 2010.

065.00—Motion for SJ by Braemer and e-Cardio; *Lifewatch* v. *Braemar* (IL) Civil Action No. 09-06001; filed Jul. 1, 2010,.

065.01—Defendants Memo ISO Motion for Summary Judgment; *Lifewatch* v. *Braemar* (IL) Civil Action No. 09-06001; filed Jul. 1, 2010.

065.02—Defendants' Statement of Undisputed Material Facts; *Lifewatch* v. *Braemar* (IL) Civil Action No. 09-06001; filed Jul. 1, 2010.

065.03—Affidavit of Robert D. Jordan; *Lifewatch* v. *Braemar* (IL) Civil Action No. 09-06001; filed Jul. 1, 2010.

065.04—Affidavit of Matthew Otto; *Lifewatch* v. *Braemar* (IL) Civil Action No. 09-06001; filed Jul. 1, 2010.

065.05—Affidavit of Paul Brinda; *Lifewatch* v. *Braemar* (IL) Civil Action No. 09-06001; filed Jul. 1, 2010.

\* cited by examiner

METHOD AND SYSTEM FOR HEALTH MONITORING

RELATED APPLICATIONS

This patent application is a continuation in part of U.S. patent application Ser. No. 11/059,791 filed on Feb. 16, 2005. This patent application is hereby incorporated by reference in its entirety.

FIELD OF THE INVENTION

The invention relates to personal health monitors and methods for health monitoring and especially to a personal health monitor that includes a cellular phone, hand-held device or other personal data assistant.

BACKGROUND OF THE INVENTION

The amount of hand-Held devices and personal data accessories, such as cellular phones, PDA and etc. has dramatically increased during the last two decades. Multiple vendors across the globe invest increasing amounts of research and development efforts to provide highly sophisticated, highly complex cellular phones. The data processing power, Graphical User Interface (GUI) capabilities and computational power of cellular phones dramatically increased during the last decade, as well as the amount of various applications that are supported by modem cellular phones.

Modem cellular phones are adapted to support multimedia applications, data related applications, as well as various games. There are various manners to download software that is later executed by the cellular phone. There are various operating systems that are supported by cellular phones (Such as: Symbian, Linux, BREW, REX, RTX, PALM, PPC2003 and etc.). By utilizing cross-operating system software tools, such as the JAVA™. software suit, applications can be developed almost regardless of the operation systems.

Cellular phone vendors have also dramatically decreased the power consumption of their cellular phones, while increasing the efficiency of cellular phone batteries, thus allowing cellular phones to operate for prolonged periods, before recharging the cellular phone battery. Nevertheless, cellular phones are periodically recharged.

FIG. 1 illustrates a prior art cellular phone 100 that includes a power connector 50 (also referred to as battery connector) for enabling an external device to charge the battery of the cellular phone, an antenna connector 52 (for connecting the cellular phone to an external antenna, such as a car mounted antenna), as well as an additional connector 56 (also referred to as system connector) for connecting the cellular phone to external devices such as audio amplifiers, hands free kit, external memory devices, communication link (RS232,USB and etc.), special data communication link, and the like. The connectors 50,52 and 56 could be combined in one or two connectors. Other prior art cellular phones, such as some Nokia™. cellular phones, include a system connector and a battery connector. U.S. Pat. No. 6,424,842 of Winstead titled "Dual function connector for cellular phones", which is incorporated herein by reference, provides a complex dual function connector that includes multiple contacts and slots.

FIG. 2 illustrates a prior art cellular phone 100. Cellular phone 100 includes an internal or external antenna 2, RF module 4, base-band processor 6, processor 8, display 10, microphone 12, speakerphone 14, loud speakers 16, analog voice and audio mixer 18, earphones 19, digital to analog converter (DAC) 20, memory module 22, integrated camera 24, USB interface 26, external memory interface 28 and keypad and joystick module 40, Optional Wireless link interface (such as: Bluetooth, WLAN, UWB (Ultra Wide Band) or other wireless link).

The internal antenna 2 can be bypassed by an external antenna 102 that is connected to cellular phone 120 via an antenna connector 54. The power supply 108 is connected on one hand to power connector 50 for recharging battery 21 and is also connected to system connector 56 to provide power from the battery 21.

Cellular phone 100 is capable of: (i) receiving RF signals from antenna 2 or external antenna 102, and vice verse; (ii) receiving audio signals from microphone 12 or an external microphone that may be a part of a hands-free/car-kit assembly; (iii) providing audio signals to loud speakers 16 or to external loud speakers; (iv) receiving information signals such as data and/or video signals from an internal camera 24, or external devices such as an external camera a computer or other cellular phone. Serial Interface, Data link interface or USB interface 26 and external memory interface 28 may receive signals via system connector 56.

Antenna 2 or external antenna 102 receives and transmits Radio Frequency (RF) signals that are provided by or received from Radio Frequency (RF) module 4. RF module 4 is connected between antenna 2 and base-band processor 6 and is able to convert RF signals to base-band signals and vice versa. Base-band processor 6, display 10 and keypad and joystick module 40, as well as integrated camera 24, USB interface 26, external memory interface 28 and digital to analog converter (DAC) 20 are controlled by and connected to processor 8 that may execute various applications. Processor 8 is controlled by a software package that may include an operating system as well as many application software, including Java engines. The software package, as well as various information are stored at memory module 22 that may include RAM as well as ROM memory cells. Memory module 22 is connected to DAC 20 and processor 8. The software package includes at least one software that is related to the transmission of information between the cellular phone and a remote station. This software is also referred to as communication related software.

Cellular phone 100 is able to receive, process and generate audio signals, by DAC 20 and base-band processor 6 that are connected to analog voice and audio mixer 18 that in turn is connected to speakerphone 14, loud speakers 16 and earphones 19. Base-band processor 6 is further connected to microphone 12. Keypad and joystick module 40 includes a multi-way Joystick and multiple keys and soft keys, positioned below display 10.

Cellular phone 100 also includes a short-range module 5, illustrated as being connected to base-band processor 6, for short-range wireless transmission and reception of information. This short-range wireless transmission and reception can be according to various standards, including the Bluetooth, WLAN, ZigB, Wi-Fi, WLAN, UWB and other standards. It is noted that module 5 can be connected to other components of the cellular phone 100. U.S. patent application 2004/0027244 of Menard, titled "Personal medical device communication system and method", which is incorporated herein by reference, provides a description of some prior art short-range and long-range transmission methods that are known in the art.

The following U.S. patent applications, that are incorporated herein by reference, describe cellular phones that are capable of applying short-range transmission: U.S. patent application 20030114106 of Miyatsu et al., titled "Mobile internet solution using Java application combined with local wireless interface"; U.S. patent application 2003/0045235 of Mooney et al., titled "Smart bluetooth interface gateway to mate a non-bluetooth wireless device with a bluetooth headset"; and U.S. patent application 20030235186 of Park titled "Internet cordless phone".

U.S. patent application 20030114106 of Miyatsu et al. describes a telecommunications system and method for downloading application software to a local communications network via an external communications network. The local communications network comprises a plurality of devices including an interface device. The interface device includes an interface for interfacing with the external communications network for downloading an application software from an application software source to the interface device via the external communications network. The local communications network preferably comprises a local wireless network, such as a Bluetooth and wireless networks, and the external communications network preferably comprises a mobile communications network for downloading application software to a mobile phone of the local wireless network.

A cellular phone that does not include a short-range transceiver, such as a bluetooth transceiver can be connected to an adapter or other means that facilitates short-range communication with the phone. U.S. patent application 2003/0045235 of Mooney et al. describes a smart bluetooth interface gateway device that allows a bluetooth headset to establish an audio connection and communicate with a conventional wireless phone (e.g., a wireless phone that does not have bluetooth installed). The connection is controlled merely by monitoring the presence of sound and tones in the audio stream from an analog audio jack of a conventional wireless phone. The smart bluetooth interface gateway device is attached to the wireless phone just as a wired headset would. Use of the wireless phone is the same as if a wired headset were plugged in.

Various methods and devices for monitoring the health of a person are known in the art. They include special hardware for gathering and processing physiological data and a wireless device utilizes for transmitting the gathered information. The special hardware is much less sophisticated and less efficient as the hardware of cellular phones. The development of dedicated hardware is usually costly.

The following U.S. patents and patent applications, which are incorporated herein by reference, provide a brief review of state of the art systems and devices: U.S. patent application 2004/0027244 of Menard, titled "Personal medical device communication system and method"; U.S. Pat. No. 5,390,238 of Kirk, et al., titled "Health support system"; U.S. Pat. No. 5,566,676 of Rosenfeldt et al., titled "Pressure data acquisition device for a patient monitoring system"; U.S. Pat. No. 5,772,586 of Heinonen et al., titled "Method for monitoring the health of a patient", U.S. Pat. No. 5,840,020 of Heinonen et al., titled "monitoring method and a monitoring equipment" and U.S. Pat. No. 5,983,193 of Heinonen et al., titled "patient's nursing apparatus and nursing system".

U.S. Pat. No. 6,366,871 titled "Personal ambulatory cellular health monitor for mobile patient" of Geva, which incorporated herein by reference describes an ambulatory patient monitoring apparatus including a portable housing including at least one physiological data input device operative to gather physiological data of the patient, location determination circuitry operative to determine geographic location information of the patient, cellular telephone communications circuitry for communicating the physiological data and the geographic location information to a central health monitoring station, voice communications circuitry. The patient conducts voice communications with a clinician at the central health monitoring station, digital signal processing circuitry for processing signals associated with any of the physiological data input device, the location determination circuitry, the cellular telephone communications circuitry, and the voice communications circuitry, and control circuitry for controlling any of the digital signal processing circuitry, the physiological data input device, the location determination circuitry, the cellular telephone communications circuitry, and the voice communications circuitry.

There is a need to provide an efficient method for health monitoring as well as an efficient personal health monitor.

SUMMARY OF THE INVENTION

The invention provides a personal health monitor that includes: a physiological data input device operative to gather physiological data; and a multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity; wherein the physiological data input device controls a transmission of the physiological data to the multi-purpose personal data accessory.

Conveniently, the physiological data input device determines whether physiological data can be sent from the physiological data input device to the multi-purpose personal data accessory.

Conveniently, the physiological data input device generates an alert in response to a determination that a transmission of physiological data to the multi-purpose personal data accessory is expected to fail.

Conveniently, the physiological data input device includes a receiver that is maintained in a low power mode during idle periods that are determined by the physiological data input device.

The invention provides a method for health monitoring, the method includes: gathering physiological data, by a physiological data input device; providing the physiological data to a multi-purpose personal data accessory using a communication link that is controlled by the physiological data input device; executing health monitoring software, by the multi-purpose personal data accessory to process the physiological data to provide processed physiological data; and transmitting the processed physiological data.

Conveniently, the method includes determining by the physiological data input device whether physiological data can be sent from the physiological data input device to the multi-purpose personal data accessory.

Conveniently, the method includes generating an alert, by the physiological data input device, in response to a determination that a transmission of physiological data to the multi-purpose personal data accessory is expected to fail.

Conveniently, the method includes maintaining a receiver of the physiological data input device in a low power mode during idle periods that are determined by the physiological data input device.

The invention provides a personal health monitor that includes: a physiological data input device operative to gather physiological data; and a multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity; wherein the multi-purpose personal data accessory is adapted to receive physiological data input device related information and to provide, in response to the physiological data input device related information, a physiological data input device instruction to the physiological data input device.

Conveniently, the physiological data input device is adapted to send configuration information to the multi-purpose personal data accessory in response to the physiological data input device instruction.

Conveniently, the physiological data input device instruction includes a configuration instruction and the physiological data input device is adapted to configure itself in response to configuration instruction.

Conveniently, the physiological data input device instruction is a physiological data retrieval instruction and the physiological data input device is adapted to send physiological data in response to the physiological data retrieval instructions.

Conveniently, the multi-purpose personal data accessory is adapted to extract the physiological data input device instruction from the physiological data input device related information.

Conveniently, the multi-purpose personal data accessory is adapted to access a remote entity; retrieve a physiological data input device instruction from the remote entity; and send the physiological data input device instruction to the physiological data input device.

Conveniently, the multi-purpose personal data accessory is adapted access a remote entity that provides web based services; provide to the remote entity an identifier included within the physiological data input device related information; and retrieve from the remote entity physiological data input device instructions.

Conveniently, the multi-purpose personal data accessory is adapted send a physiological data input device instruction that is selected from a list consisting of physiological data retrieval instructions and configuration instructions.

The invention provides a method for health monitoring, the method includes: gathering physiological data, by a physiological data input device; providing the physiological data to a multi-purpose personal data accessory; executing health monitoring software, by the multi-purpose personal data accessory to process the physiological data to provide processed physiological data; transmitting the processed physiological data; receiving physiological data input device related information by the multi-purpose personal data accessory; and providing, in response to the physiological data input device related information, a physiological data input device instruction to the physiological data input device.

Conveniently, the method includes sending configuration information, by the physiological data input device, to the multi-purpose personal data accessory in response to the physiological data input device instruction.

Conveniently, the physiological data input device instruction includes a configuration instruction and the method includes configuring the physiological data input device in response to the configuration instruction.

Conveniently, the physiological data input device related information includes a physiological data retrieval instruction and the method includes sending physiological data from the physiological data input device in response to the physiological data retrieval instruction.

Conveniently, the method includes extracting the physiological data input device instruction by the multi-purpose personal data accessory.

Conveniently, the method includes accessing a remote entity; retrieving a physiological data input device instruction from the remote entity; and sending the physiological data input device instruction to the physiological data input device.

Conveniently, the method includes accessing a remote entity that provides web based services; providing to the remote entity an identifier included within the physiological data input device related information; and retrieving from the remote entity physiological data input device instructions.

Conveniently, the method includes sending, by the multi-purpose personal data accessory, a physiological data input device instruction that is selected from a list consisting of physiological data retrieval instructions and configuration instructions.

BRIEF DESCRIPTION OF THE DRAWINGS

Further features and advantages of the invention will be apparent from the description below. The invention is herein described, by way of example only, with reference to the accompanying drawings, wherein:

FIG. 8 illustrates a plug-in unit, according to an embodiment of the invention;

DETAILED DESCRIPTION OF THE DRAWINGS

The following description mainly refers to monitoring a health of a person. It is noted that this method and monitors can be applied to track multiple persons simultaneously, such as tracking the performances of a team of players.

The following description also refers to a cellular phone that can be provided with health monitoring software that enables the cellular phone to process physiological data, and especially without any addition of complex hardware, such as additional processors. It is noted that the invention can be applied to other multi-task and/or multi-purpose accessories, especially personal data accessories (PDAs) other that cellular phones that in turn may include palm-computers and the like.

The following description describes various transmitters, such as short-range transmitters and long-range transmitters. Each transmitter is associated with a corresponding receiver, but for simplicity of explanation a larger emphasis was placed upon the transmitters.

It is noted that according to various embodiments of the invention the cellular phone (or other personal data accessory) can include a short-range transmitted for transmitting information (such as instructions) to various components (such as physiological data input devices, adapters and the like) that are equipped with corresponding short-range receivers.

Figure 1:
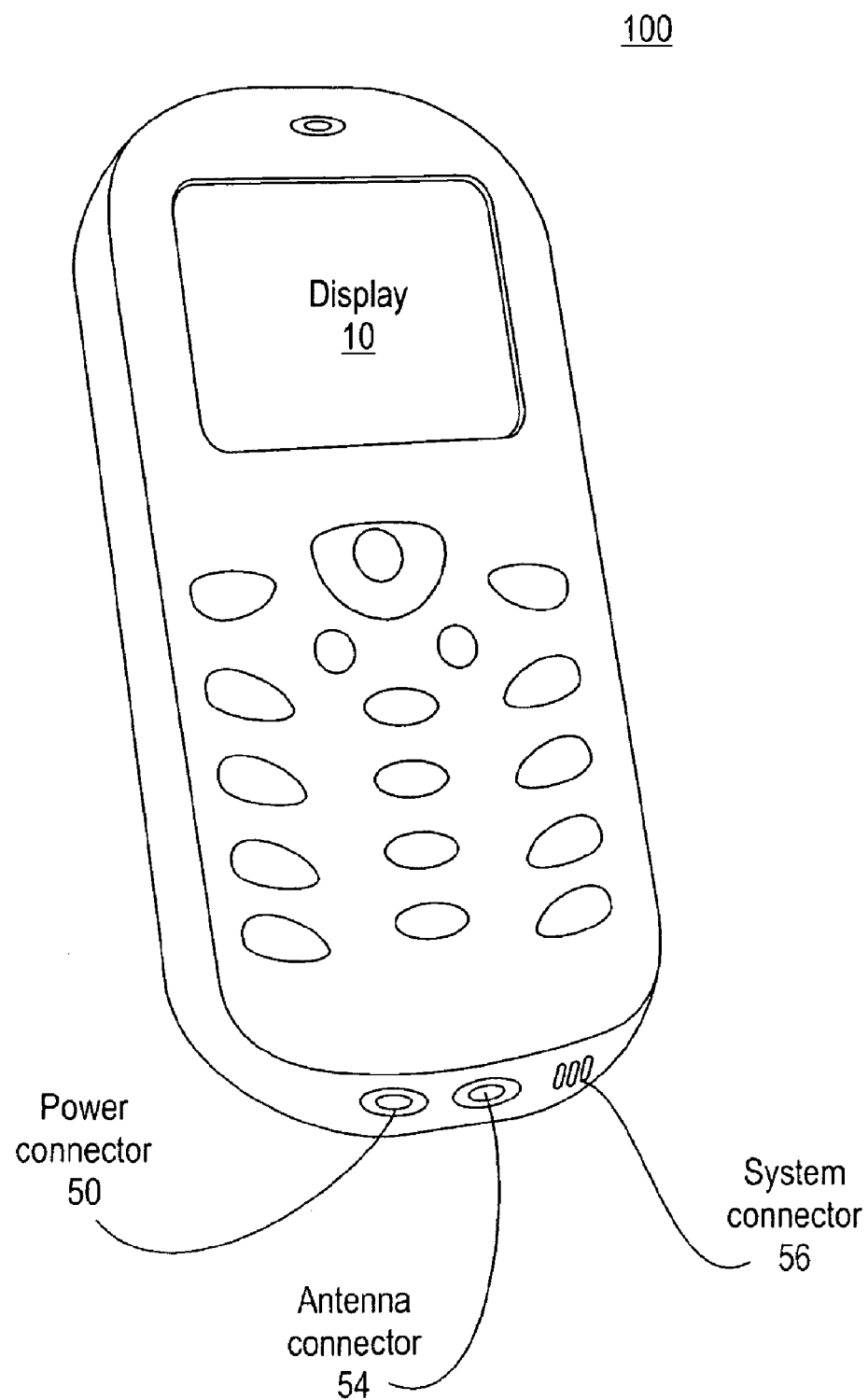
FIGS. 1-2 are schematic diagrams of a prior art cellular phone.
Figure 2:
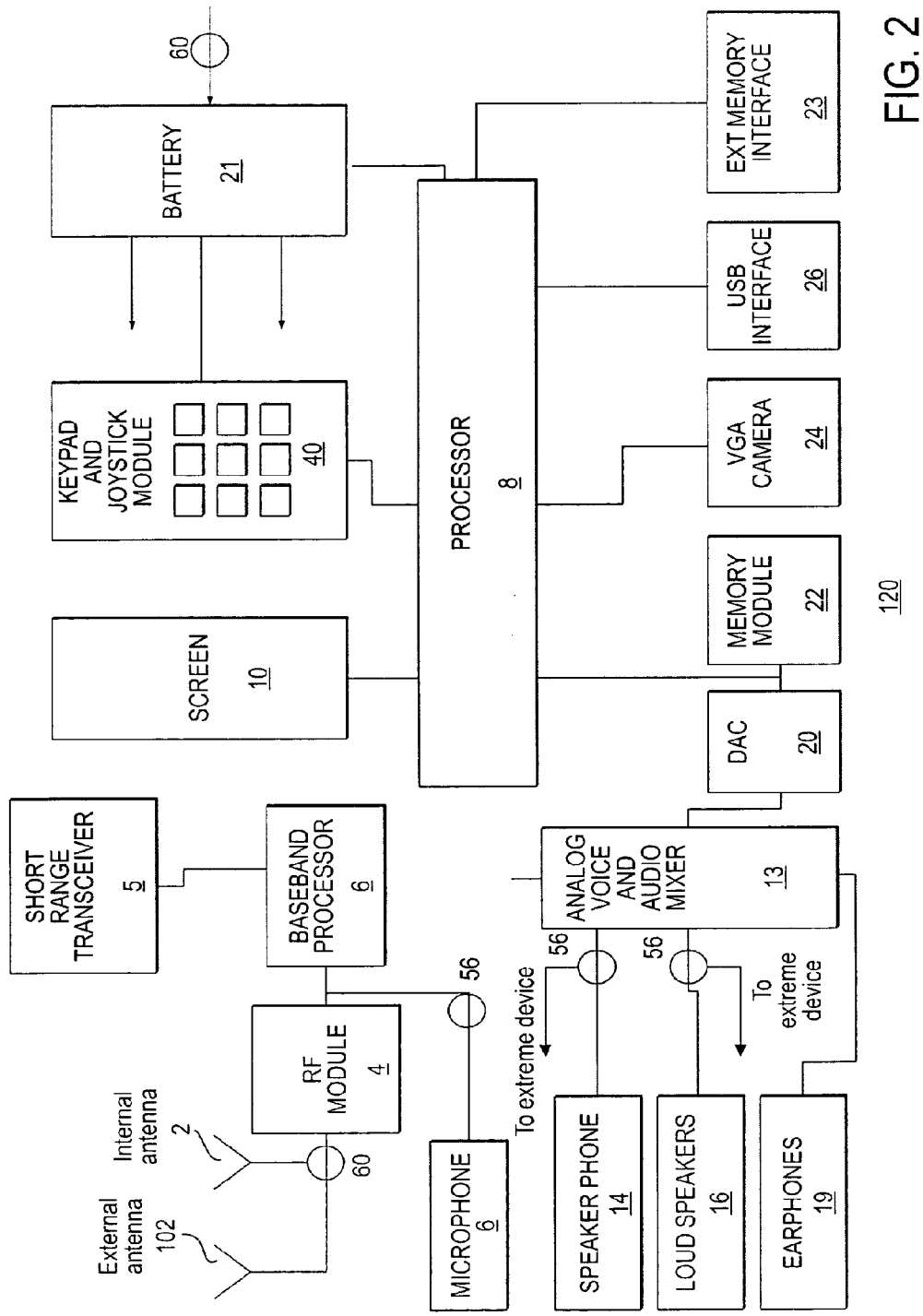

The cellular phone that is referred to in the following figures can resemble the prior art cellular phone 100 of FIGS. 1 and 2 but in addition has health monitoring software for processing physiological data.

FIGS. 3-6 are schematic illustrations of a personal health monitor 1 that includes one or more physiological data input devices and a cellular phone (or another PDA), according to various embodiment of the invention. Each figure illustrates one or more physiological data input devices that may include at least one of the following devices: an electrocardiograph (ECG) input device, a device for monitoring blood oxygen saturation, a device for monitoring respiration, a device for monitoring blood glucose, a device for monitoring blood pressure, a device for monitoring lung function, a device for monitoring SpO2 saturation, a device for monitoring temperature, a device for fat analysis, a drug dispenser, drug taking reminder, a container device, a fetal hart rate monitor device for pregnancy women, EEG device and the like. Each physiological data input device includes at least one sensor and may also include an analog component such as an analog amplifier, an analog comparator and the like. Such a physiological data input device may also include an analog to digital converter (ADC), although such an ADC is typically located within another component that is connected to the physiological data input device.

Figure 3:
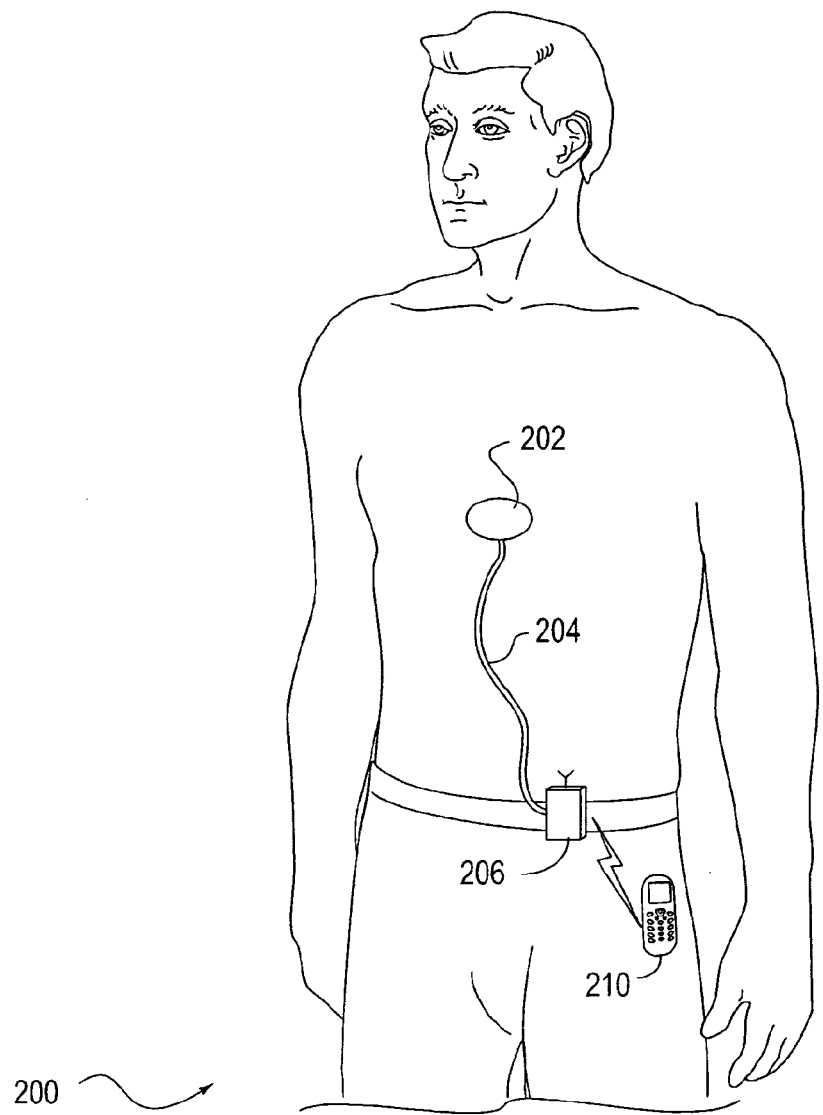
FIGS. 3-6 and 8 are schematic illustrations of a person that is wearing single or multiple physiological data input devices and also carries a cellular phone or PDA, according to an embodiment of the invention.

FIG. 3 illustrates a person 200 that is wearing a physiological data input device 202 operative to gather physiological data. In this figure the physiological data input device 202 are connected to person 200 by a sticker, but this is not necessarily so. The physiological input device 202 can be connected to an elastic stripe or some type of belt that in turn is worn by person 200.

The physiological data input device 202 is connected by wire 204 to a short-range transmitter 206 or the device 202 is embedded in the 206. The short-range transmitter 206 is adapted to wirelessly transmit the gathered physiological data to cellular phone 210 or other personal data accessory. Either the physiological data input device 202 or the short-range transmitter 206 include a analog to digital converter for providing a digital stream of signals representative of the physiological condition of the person 200.

According to various embodiments of the invention the short-range transmitter 206 transmits the physiological data to the cellular phone 210 in bursts. Burst transmitters are known in the art and do not require additional explanation. Typically, such a transmitter includes one or more buffers or other memory components (such as a stack, multiple memory cells and the like), for storing data before being transmitted in bursts. The bursts can be transmitted whenever a certain transmission condition is fulfilled (for example—the one or more buffers are full), or in a predefined manner. The burst rate is usually responsive to a ratio between the sampling-rate of the physiological data provided by the physiological data input device and between the transmission bit-rate. Typically the sampling-rate is at selected such as to fulfill the Nyquist condition.

The short-range transmitter 206 can apply error corrections algorithms, such as CRC, in order to compensate for possible errors in the short-range transmission. The short-range transmission can be implemented in a standard manner, for example according to the Bluetooth standard, but this is not necessarily so.

Figure 5:
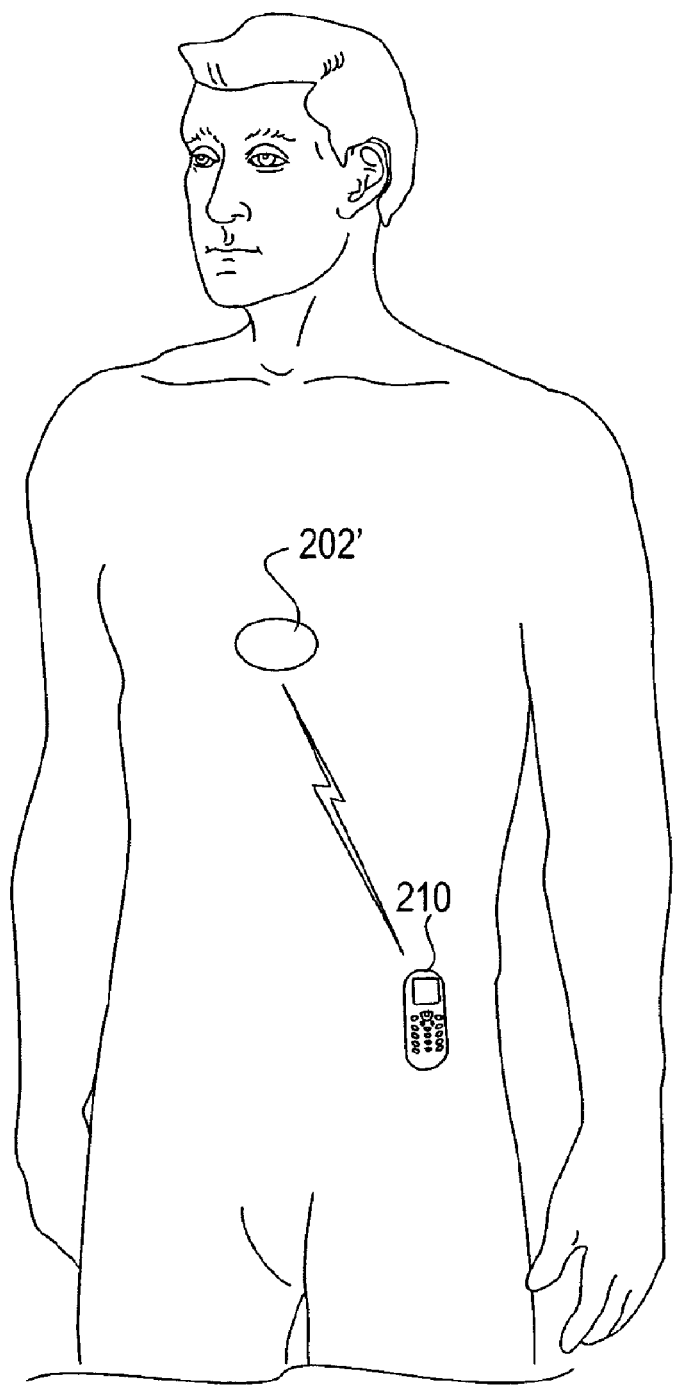

It is further noted that a short-range transmission circuitry can reside within the cellular phone 210 or be attached to the phone by means of a short-range transmission adapter 222, as illustrated in FIG. 5.

Figure 4:
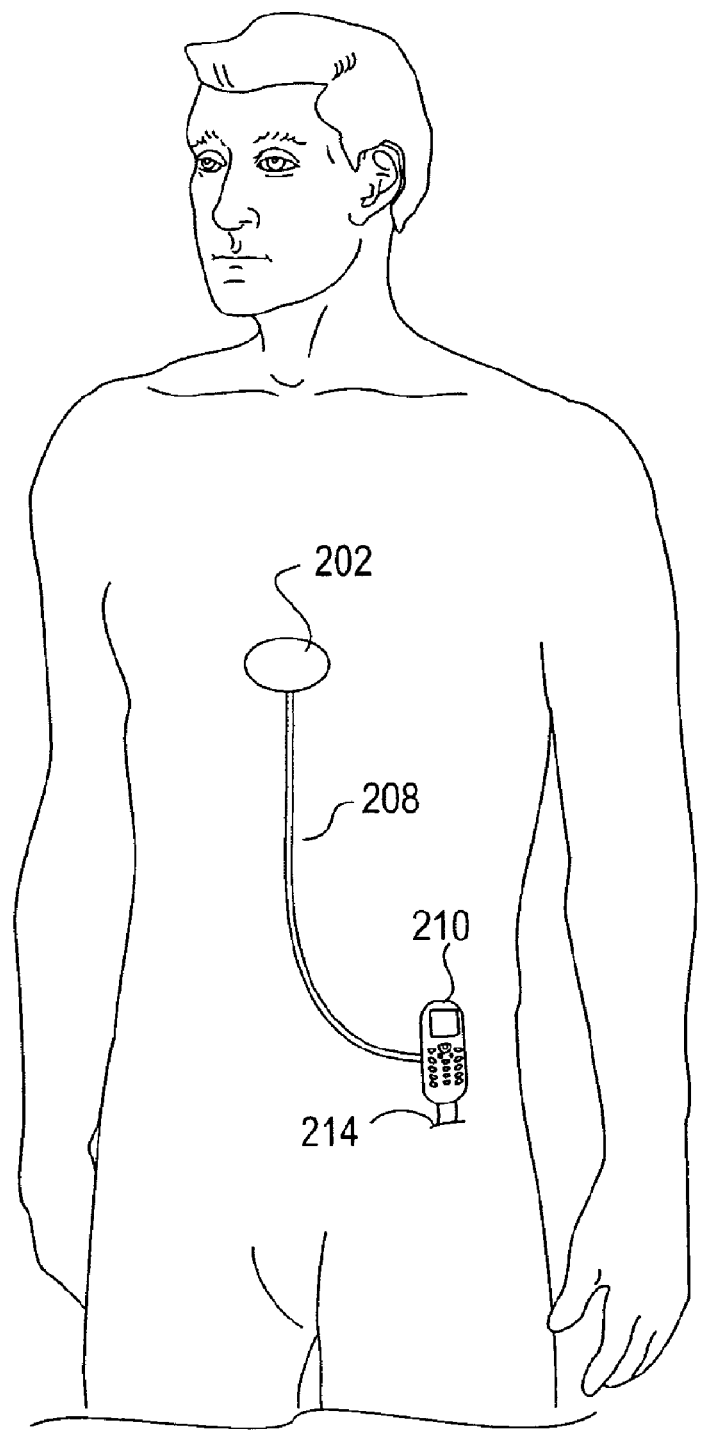

FIG. 4 illustrates another embodiment of the invention in which the physiological data input device 202 is connected via wire 208 to the cellular phone 210 via an additional component, such as protocol adapter 212. The additional component can include a signal converter, adapted to convert signals arriving from the physiological data input device 202 to a format that is recognized by the mobile phone 210. The converter may include an analog to digital converter, communication protocol adapted and the like.

FIG. 5 illustrates another embodiment of the invention in which the physiological data input devices 202' have wireless short-range transmission capabilities and are capable of short-range communication with the cellular phone 210. Electrodes that include wireless transmission capabilities are known in the art and are described, for example, at U.S. Pat. No. 6,577,893 of Besson et al., titled "wireless medical diagnosis and monitoring equipment" which is incorporated herein by reference.

Figure 6:
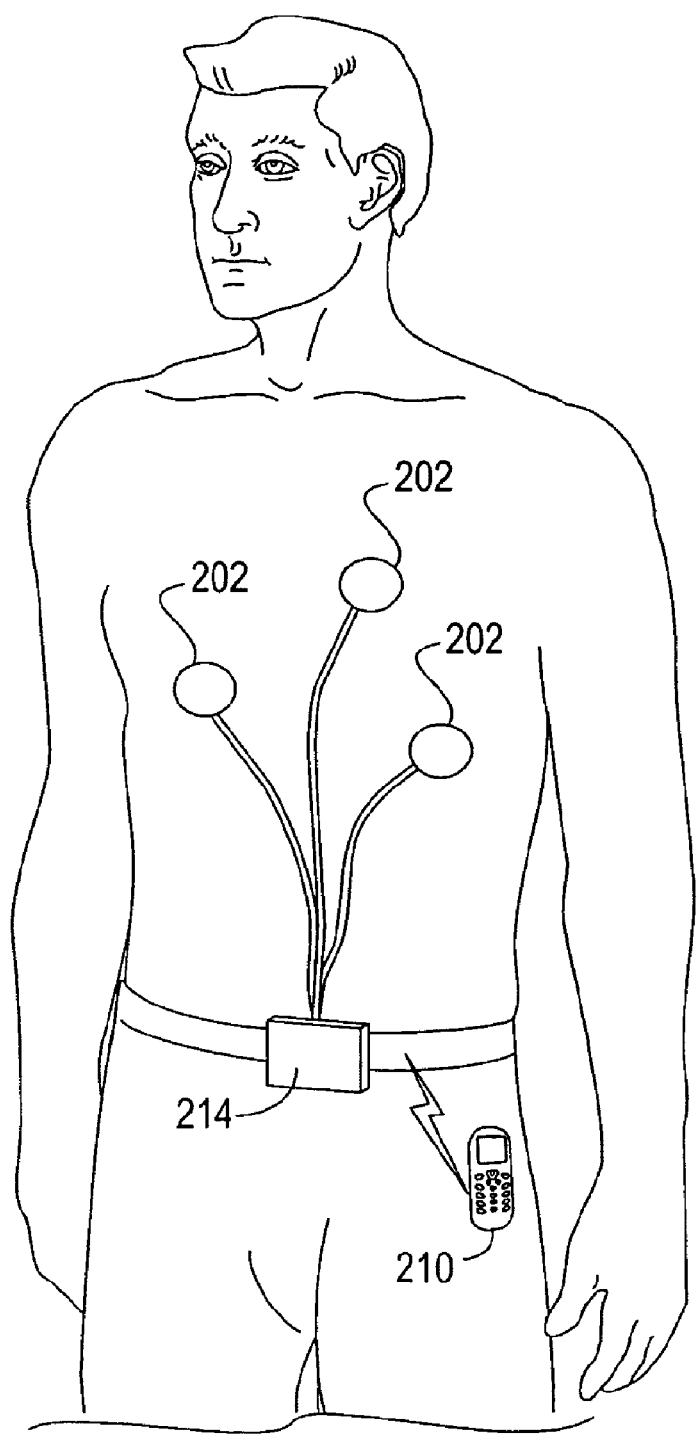

FIG. 6 illustrates another embodiment of the invention in which multiple physiological input devices 202 are connected to an adapter 214 that in turn may generate a multiplexed signal stream that includes signals from one or more of the multiple physiological input devices 202. The adapter 214 conveniently includes one or more analog to digital converters, buffers and a short-range transmitter 206. According to another embodiment of the invention the adapter 214 includes an interface, instead of the short-range transmitter, that is connected to a wire that in turn is connected to cellular phone 210.

According to an embodiment of the invention the adaptor 214 can include a medical sub-system that facilitates the connection of multiple physiological input devices 202 of various types. Such a medical sub-system is described, for example, in U.S. Pat. No. 6,366,871 titled "Personal ambulatory cellular health monitor for mobile patient" of Geva, which incorporated herein by reference.

Figure 7:
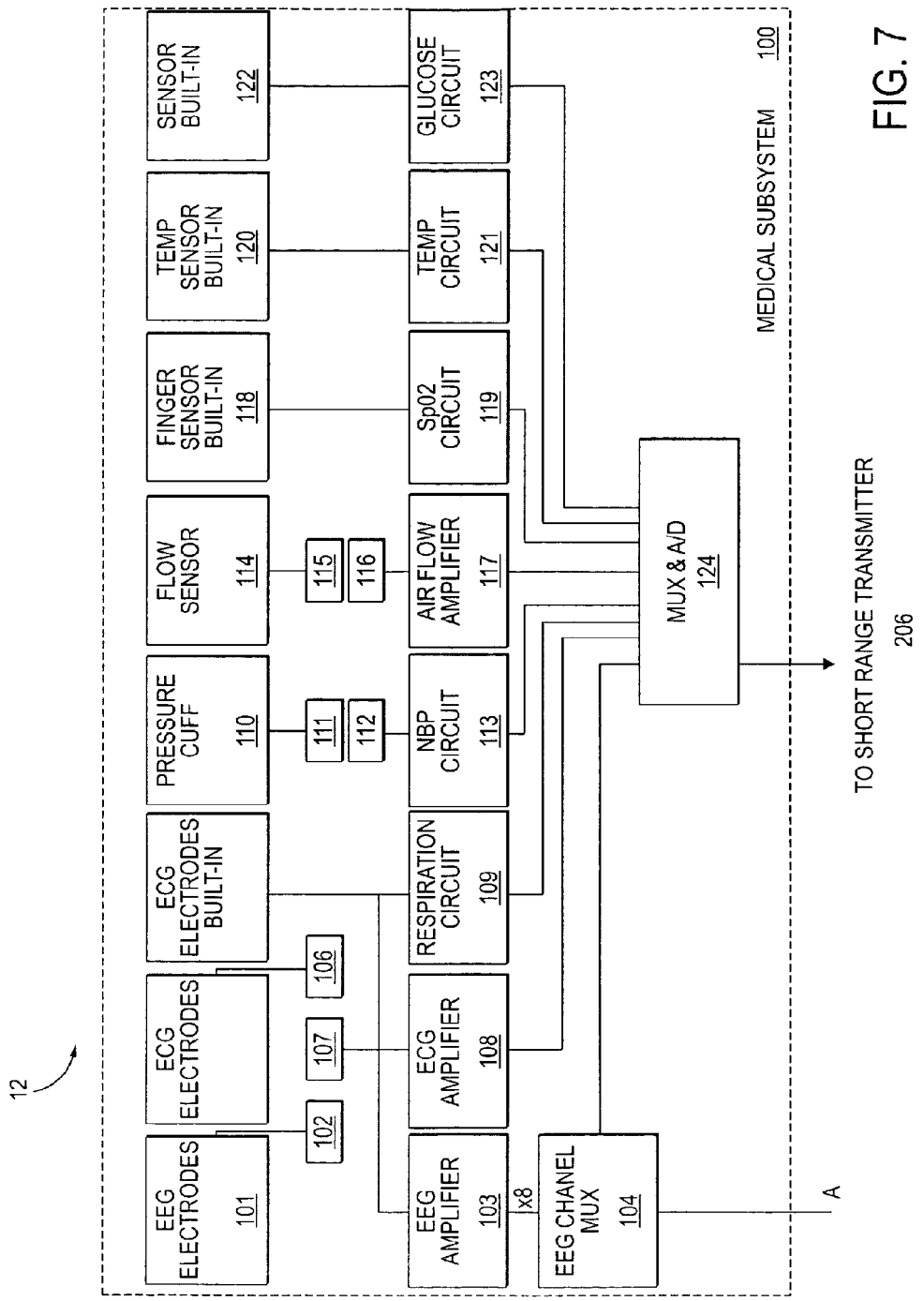
FIG. 7 is a schematic illustration of a medical sub-system.

FIG. 7 illustrates a medical sub-system 100 that includes a multiplexing and analog to digital converter 124 that is connected to multiple analog components such as EEG amplifier 103, ECG amplifier, respiration circuit 109, NBP circuit 113, air flow amplifier 117, SpO2 circuit 119, temperature circuit 121 and glucose circuit 123 that in turn are connected to various sensors such as EEG electrodes 101, ECG electrodes 105, a pressure cuff 110 for measuring NIBP, and an air flow sensor 114 for measuring spirometry, finger sensor 118, temperature sensor 120 and glucose sensor 122. The sensors can be connected directly to the analog circuits or via various connectors or plugs, such as plugs 102, 106, 107, 115, as well as via EEG multiplexer 104. Some of the plugs, such as plug 107, can be used for connecting a first sensor or another sensor, and the connector includes circuitry for determining which sensor is actually connected to the plug.

According to various embodiments of the invention hardware components, such as adaptor 214, physiological input device 202, and alternatively or additionally, short-range transmitter 206 that are connected to the cellular phone by a wire, the cellular phone 210 can be utilized for supplying energy to the wired components. For example, the battery of the cellular phone can be connected, via a wire and/or a connector such as system connector 56 of FIG. 1.

Figure 8:
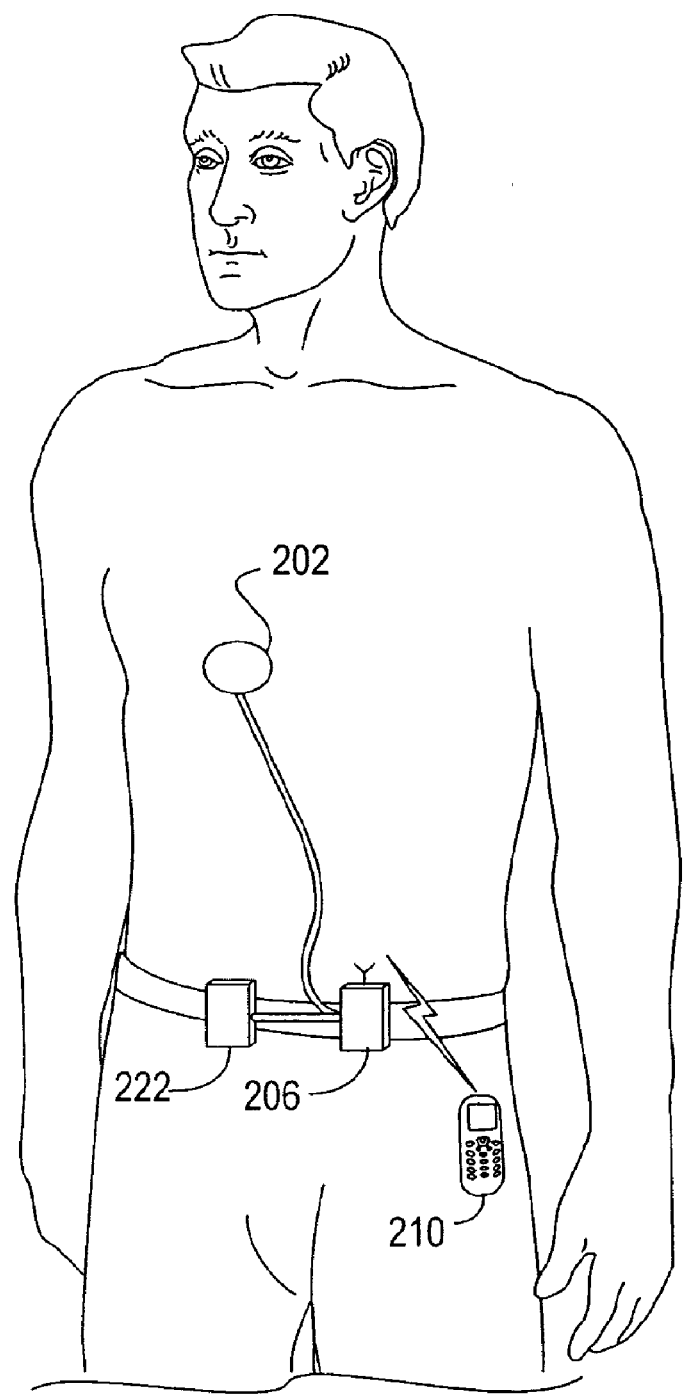

FIG. 8 illustrates another embodiment of the invention in which the person 200 carries one or more physiological data input devices, such as device 202, as well as a personal location subsystem 222 capable of determining a location of the person 200. Thus, location information is also sent to the cellular phone 210 and then long-range transmitted to a remote station (not shown).

The personal location subsystem 222 determines the location of person 200. It usually includes known location determination circuitry such as GPS components including a GPS receiver and a filter that is tuned to a known GPS frequency for CPS satellite communication via a built-in antenna. The personal location subsystem 222 conveniently receives a pseudo range (PR) and pseudo range dot (PRD) from GPS satellites in communication range. The GPS receiver preferably operates in aided mode enabling "snapshot" operation as is known in GPS systems. The position of person 200 and velocity data is conveniently transmitted via a short-range transmitter 206 and to cellular phone 210.

The location of person 200 can be transmitted in predetermined events (Such as location, Distance, Velocity and such as system initialization) or automatically.

Figure 9:
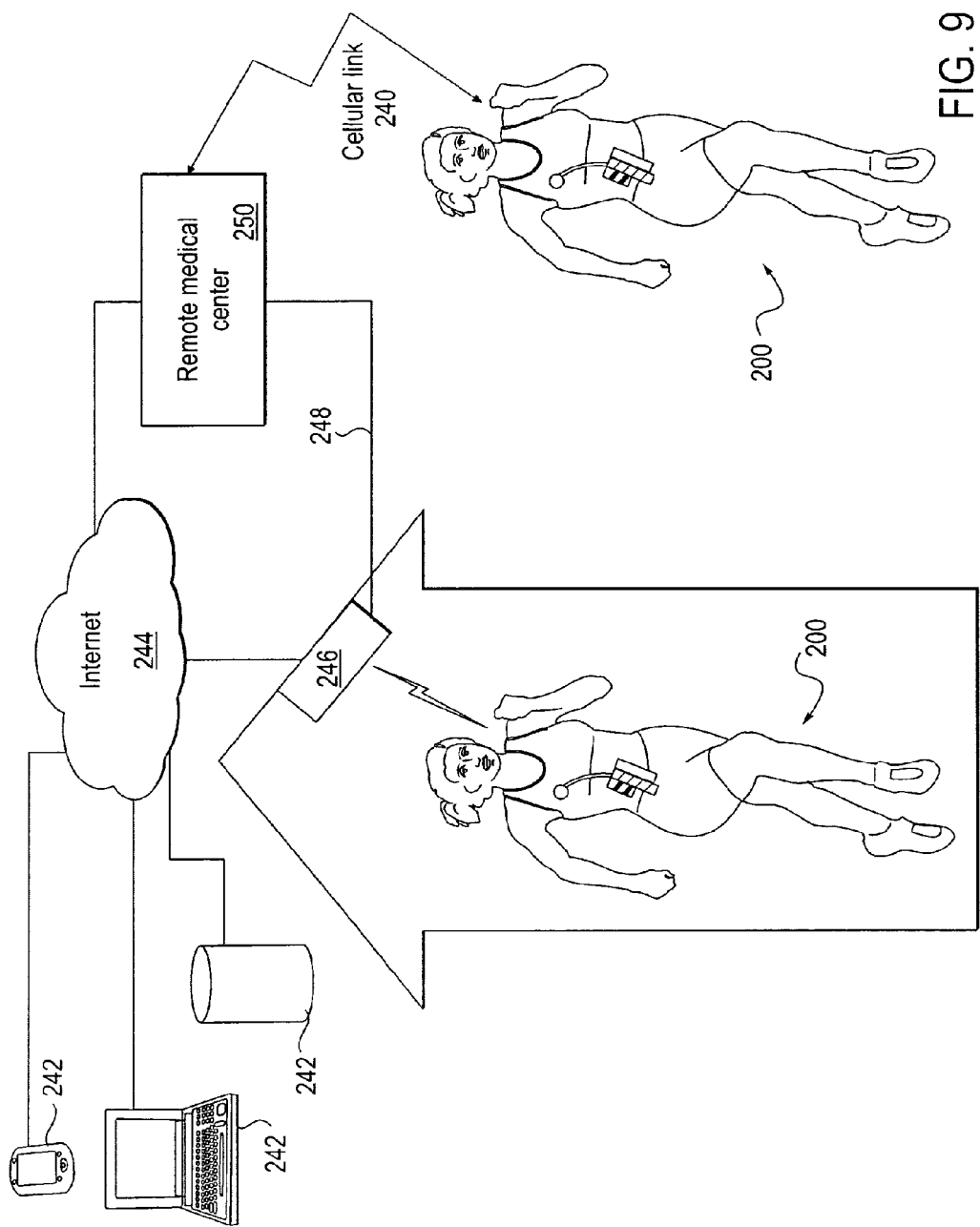
FIG. 9 illustrates a medical center as well as devices for gathering, processing and transmitting physiological data, according to an embodiment of the invention.

Reference is now made to FIG. 9 which is a simplified block diagram illustrating end-to-end communication between a physiological data input devices 202 worn by two persons 200 and 201 and between a remote medical center 230, according to an embodiment of the invention.

The physiological data input device 202 worn by the first person 200 is connected by wire 204 to a short-range transmitter 206. The short-range transmitter 206 transmitted physiological data to cellular phone 210 where the data is processed. The cellular phone 210 is capable of determining whether to transmit the processed physiological data, to transmit a portion of the data or not to transmit it at all.

The cellular phone 210 is connected over a cellular network that is represented by wireless link 240 or via another network such as Internet 244 to a remote medial center 250. The remote medical station 250 can be connected to various databases and accessories 242 via another network such as the Internet 244.

The second person 201 also wears a physiological data input device 202 that is connected by wire 204 to a short-range transmitter 206 that in turn transmits physiological data towards short-range receivers 246 that are capable of transmitting the data to the remote medical center 250 via a WLAN, Cable TV, Satellite TV, CCTV, Telephone line, GSM/GPRS, CDMA, TDMA, iTV, Internet and other network represented by link 248. In this scenario the gathered physiological data can be analyzed by the short-range receiver 246 (or more specifically by a processor that is connected to the receiver). In case of the cable TV, CCTV, ITV, Satellite TV and etc the TV device might be the GUI interface device for user.

Various remote medical centers are also known as central medical monitoring stations and are known in the art. Such a center is described at U.S. Pat. No. 6,366,871 titled "Personal ambulatory cellular health monitor for mobile patient" of Geva, which incorporated herein by reference. It is noted that Geva describes a monitor that is capable of vocal communication with the person, and this feature can be implemented by using the cellular phone 210.

The physiological data input devices 202 and the cellular phone 210 can operate in various modes that include: (i) Event recording activated by the person, either at the person initiative, a third party (such as a clinician) initiative, or pursuant to an alarm, where the person performs one or more tests and transmits processed physiological data to the remote medical center 230. In this mode the remote medical center 230 may be contacted at the beginning of the event for transmission of processed physiological data during the event or at the conclusion of the testing. (ii) Continuous monitoring where physiological data are captured periodically and transmitted to the remote medical center 230. Continuous monitoring may be provided in any of the following ways: Patient-activated event recorder where processed pre-event/event/post-event data is transmitted to the remote medical center 230; Device-activated event recorder where physiological data is detected which fall outside preset parameters; Holter-mode where processed physiological data is transmitted automatically when a buffer of an adaptor or a memory space of the cellular phone allocated for storing the processed (or non-processed) physiological data becomes full; and Holter-mode where processed physiological data is transmitted by a person at any time.

Figure 10:
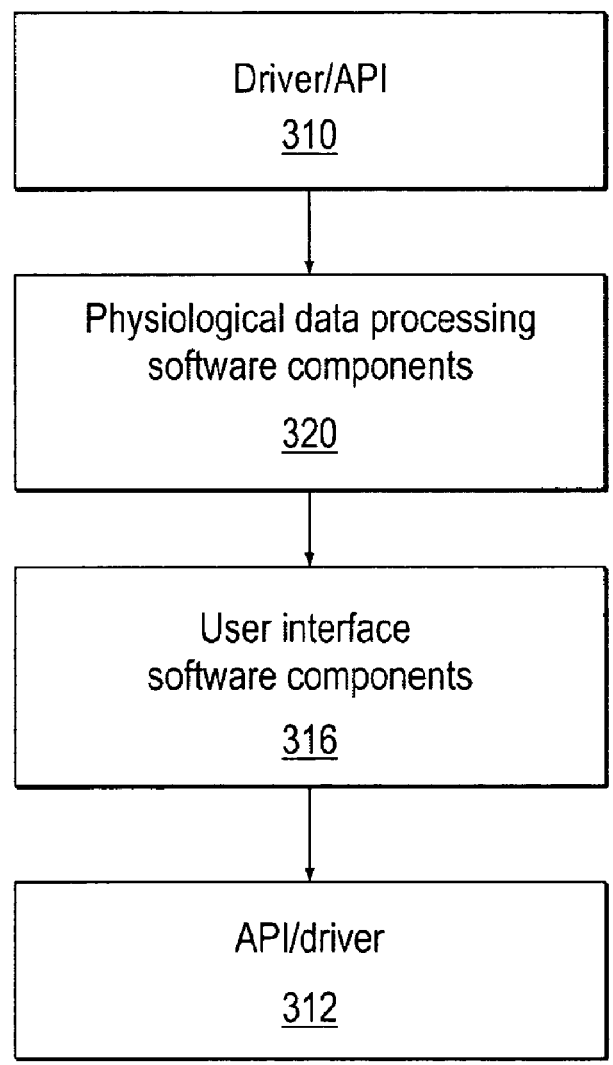
FIG. 10 illustrates a example of the configuration of a health monitoring software that is implemented in the Cellular phone or PDA, according to an embodiment of the invention.

FIG. 10 illustrates a configuration of the health monitoring software 300, according to an embodiment of the invention. The health monitoring software 300 includes a driver/API 310 between the cellular phone and the wireless network for long-range transmission of processed physiological data, for example in accordance to GPRS, CDMA, GSM and the like. The health monitoring software also includes an API or driver 312 for the short-range or wired data link through which the cellular phone receives the physiological data. The health monitoring software also includes physiological data processing software components 314 as well as user interface software components 316.

It is noted that other software configurations can be utilized. It is also noted that the drivers/API can be a part of the non-medical software components of the cellular phone. For example, a cellular phone that has an embedded short-range receiver includes a short-range communication software module, regardless the presence of the medical application.

The user interface component 316 can apply various known in the art techniques, such as but not limited to a menu based interface in which the person can make various selections between various options that are displayed over the display of the cellular phone. It is also noted that given the advanced multimedia capabilities of modem phones the user interface can also include receiving vocal input and outputting vocal output.

The physiological data processing software component 314 can apply various well-known algorithms for processing the physiological data.

For example, the software can enable the personal health monitor 1 to perform at least one of the following: (i) automatic arrhythmia analysis in different quantization levels (up to 8 bits) in different sampling rates (including 100 Hz), (ii) perform one lead arrhythmia detection in various noise conditions, (iii) perform continuous automatic adaptation to the patient normal heartbeat morphology, (iv) perform continuous real time processing and provide, on request, a summery of the patient heart condition, (v) perform environmental and adaptive noise/movement artifact elimination, (vi) enable the person to adjust the definitions of the pathology sequences detected by the system (for example the number of consecutive PVC heartbeats and the minimum heart rate to define VT) and others.

The health monitoring software 300 can detect various medical events and determine a medical state of a person. In some operational modes out of the mentioned above modes an occurrence of a medical event can initiate a transmission of processed physiological data and even cause the cellular phone 210 to generate an audio an/or visual alarm message. This health monitoring software 300 can process received physiological data to determine the occurrence of the following: isolated premature ventricular contraction (PVC), isolated premature atrial contraction (PAC), bigeminy, trigeminy, couplet, bradycardia, tachycardia, ventricular tachycardia, supra-ventricular tachycardia. The software can detect a morphology change, perform PR, ST, QRS, QT segmentation, Heart Rate Variability (HRV) analysis and QT Analysis, and the like. According to various embodiments of the invention the health monitoring software 300 can cause the cellular phone to display graphs or other visual representations of the monitored physiological data. According to an embodiment of the invention the cellular phone 210 is capable of retrieving medical information related to the person, and displaying the retrieved medical information.

Figure 11:
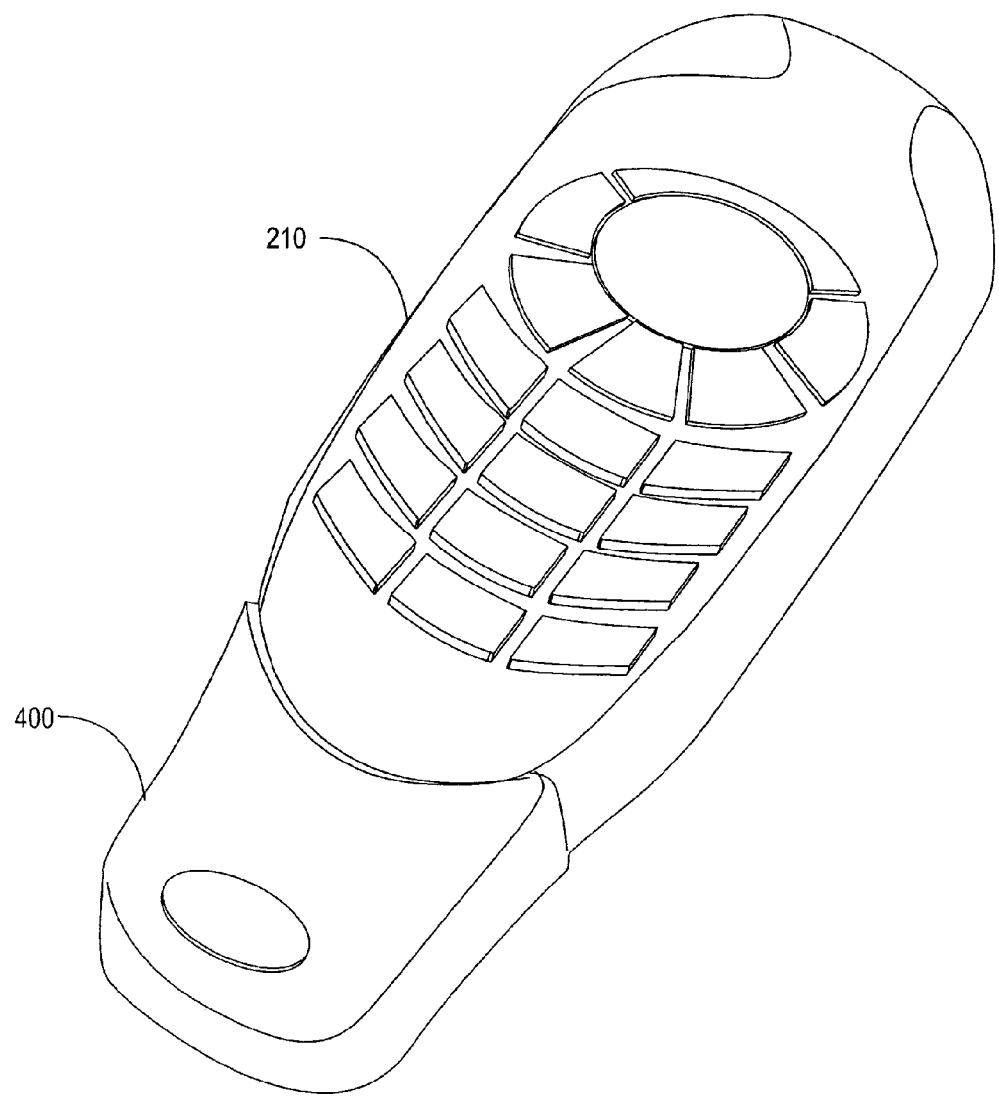
FIG. 11 illustrates a plug-in device that is detachably connected to cellular phone, according to an embodiment of the invention.

In order to prevent unauthorized use of such a feature the cellular phone can apply various measures such as password protection, biometric measures and the like. FIG. 11 illustrates a plug-in device 400 that is detachably connected to cellular phone 210, according to an embodiment of the invention. The plug-in device can gather one or more type of physiological data, and can include one or more of the previously mentioned sensors, analog circuitry and even can include a multiplexer and analog to digital converter and cable/direct connection and communication to the Cellular Phone that is based on the micro controller. The following scenarios provide example of the interaction between the person and the monitor. For simplicity of explanation we refer to the plug-in device of FIG. 11 but this also applies to the previously mentioned configurations. A sugar level test includes the following stages: the person initialized the test by pressing a certain button, the person inserts a strip in a strip chamber of the plug-in device, the person places a drop of blood on the strip, the plug in sends physiological data reflecting the content of that drop to the cellular phone 210 that in turn processes the gathered physiological data to determine the level of sugar. The person can also view pervious sugar level tests, for example during a time period defined by the person. The cellular phone can display a history trend graph of results with normal level highlighted in a different color.

An ECG test can include the following stages: the person presses on a certain button, the person places his fingers on an electrode, the personal physiological monitor retrieves and processes physiological data to determine the stage of the person, a cardiogram is displayed on the monitor of the cellular phone. The person can see the result of previous tests and/or determine whether to save the results of the current test, and the like.

Figure 12:
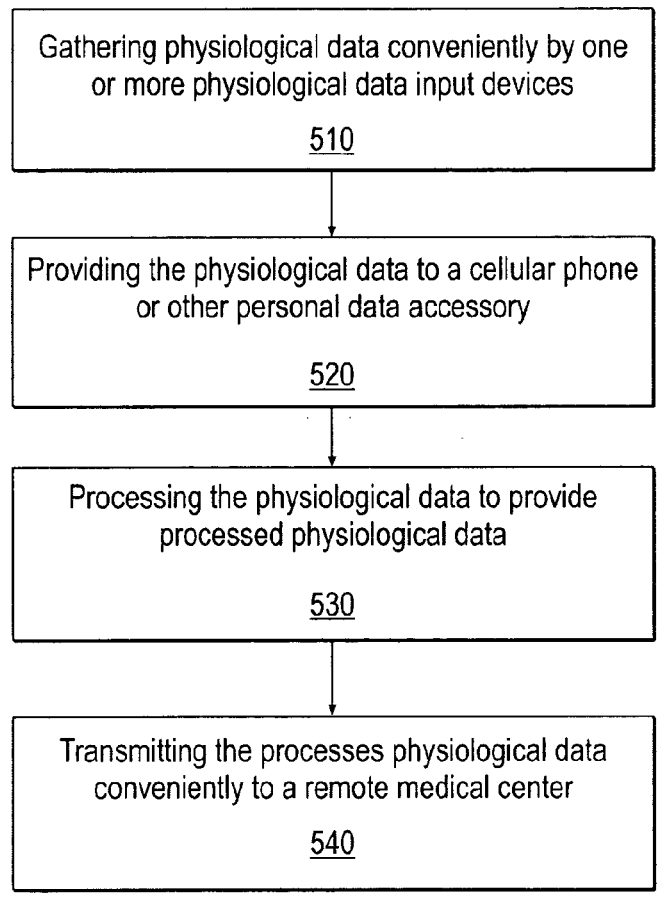
FIG. 12 is a flow chart of method for health monitoring, according to an embodiment of the invention.

FIG. 12 is a flow chart of method 500 for health monitoring, according to an embodiment of the invention.

Method 500 starts by stage 510 of gathering physiological data, conveniently by one or more physiological data input devices. Conveniently, one of the configurations illustrated at FIGS. 3-6, 8 can be used. Data is gathered by one or more physiological data input device.

Stage 510 is followed by stage 520 of providing the physiological data to a cellular phone or other personal data accessory. This stage can include short-range transmission of the physiological data, wire based transmission and the like.

Stage 520 is followed by stage 530 of processing the physiological data to provide processed physiological data. Stage 530 may include applying various well-known algorithms, such as those previously mentioned.

Stage 530 is followed by stage 540 of transmitting the processes physiological data, conveniently to a remote medical center. This stage usually includes long-range transmission of the information.

According to another embodiment of the invention the analyzed physiological data as well as optional information from the personal location can be sent to a center, such as medical center 250 and may be utilized for providing and controlling a diet and/or exercise regime. For example, a person starts to run and begins to transmit location information. This location information along with the timing of its transmission can be used to determine if the person runs, the distance that he runs and even an estimated calorie consumed during this running session. This data can be added to physiological data such as heart rate and fat measurement to provide an indication about the progress of the person in a diet physical fitness regime. The cellular phone 210 can be used to process above mentioned data and display the person indications about scheduled meals, physical exercises, and the like or the above data can be processed in medical center 250 and the cellular phone 210 can be used to send the person indications about scheduled meals, physical exercises, and the like.

Figure 13:
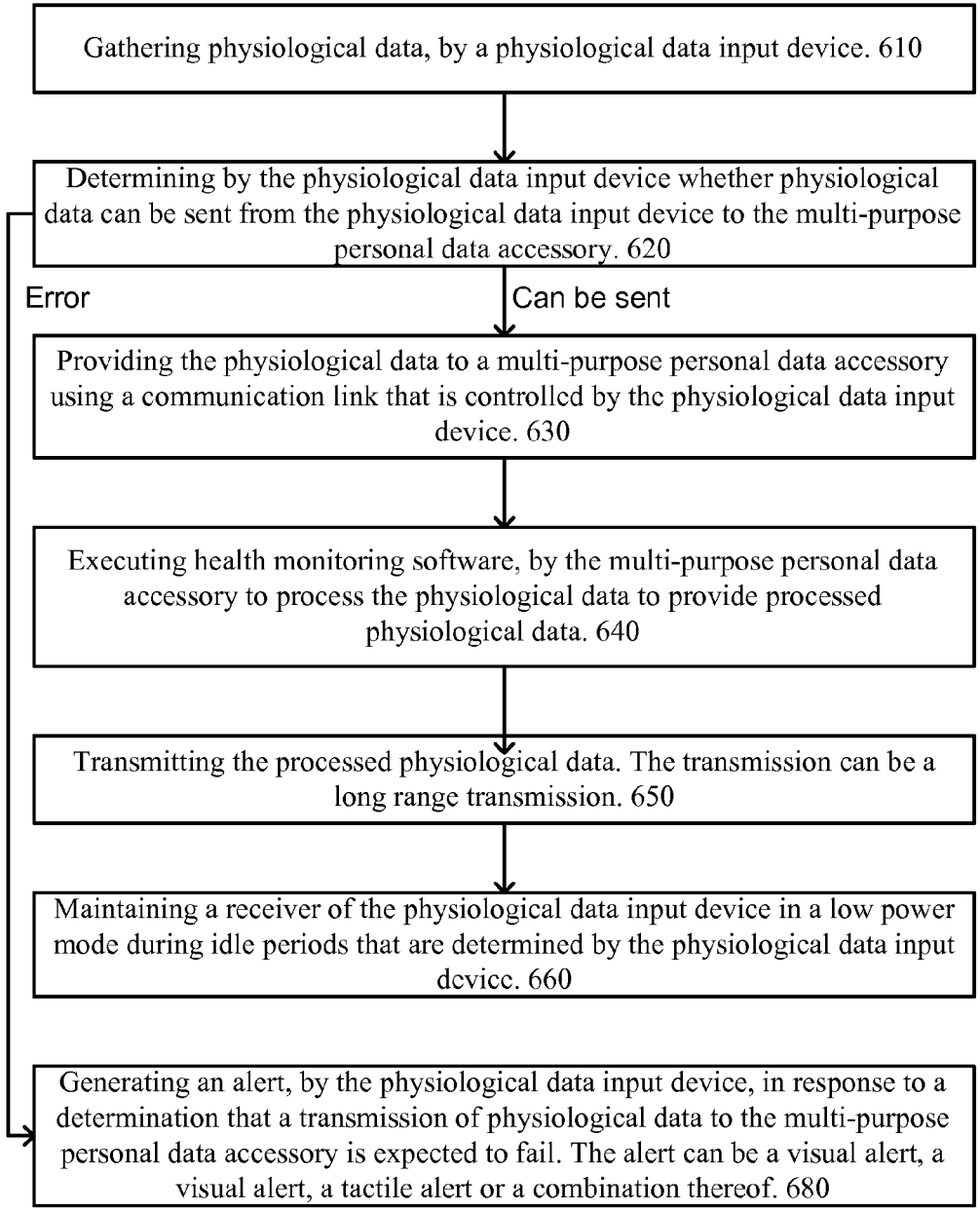
FIG. 13 illustrates a flow chart of a method for health monitoring according to another embodiment of the invention.

FIG. 13 illustrates a flow chart of method 600 for health monitoring according to another embodiment of the invention.

Method 600 starts by stage 610 of gathering physiological data, by a physiological data input device. Stage 610 is conveniently equivalent to stage 510 of FIG. 12. The physiological data input device can be device 202 of either one of FIGS. 4, 6, 8 and 9, can be connected to adapter 214 of FIG. 6 (that includes a short range receiver as well as a short range transmitter), can be plug-in device 400 of FIG. 11, can include medical sub-system 100 of FIG. 7, and the like.

Stage 610 is followed by stage 620 of determining by the physiological data input device whether physiological data can be sent from the physiological data input device to the multi-purpose personal data accessory. Conveniently, the determination can be responsive to one or more previous transmission attempts, to results of monitoring (by the physiological data input device) a communication link between the physiological data input device to the multi-purpose personal data accessory, to communication error indications sent by the multi-purpose personal data accessory and the like.

If the physiological data input device determines that it can successfully transmit the physiological data to the multi-purpose personal data accessory then stage 620 is followed by stage 630, else stage 620 is followed by stage 680.

Stage 630 includes providing the physiological data to a multi-purpose personal data accessory using a communication link that is controlled by the physiological data input device. The multi-purpose personal data accessory can be a mobile phone (such as mobile phone 210 of FIGS. 3, 4, 5, 6 and 8), can be a PDA, and the like. It is capable of being used for purposes that differ from the health monitoring.

Stage 630 is followed by stage 640 of executing health monitoring software, by the multi-purpose personal data accessory to process the physiological data to provide processed physiological data.

Stage 640 is followed by stage 650 of transmitting the processed physiological data. The transmission can be a long range transmission.

Method 600 also includes stage 660 of maintaining a receiver of the physiological data input device in a low power mode during idle periods that are determined by the physiological data input device. This can reduce the power consumption of the physiological data input device, as it is not expected to constantly look for transmissions from the multi-purpose personal data accessory.

Stage 680 includes generating an alert, by the physiological data input device, in response to a determination that a transmission of physiological data to the multi-purpose personal data accessory is expected to fail. The alert can be a visual alert, a visual alert, a tactile alert or a combination thereof. For example, the physiological data input device can vibrate or send an alert that requests the person that wears the physiological data input device to place the physiological data input device within a reception range from the multi-purpose personal data accessory.

Figure 14:
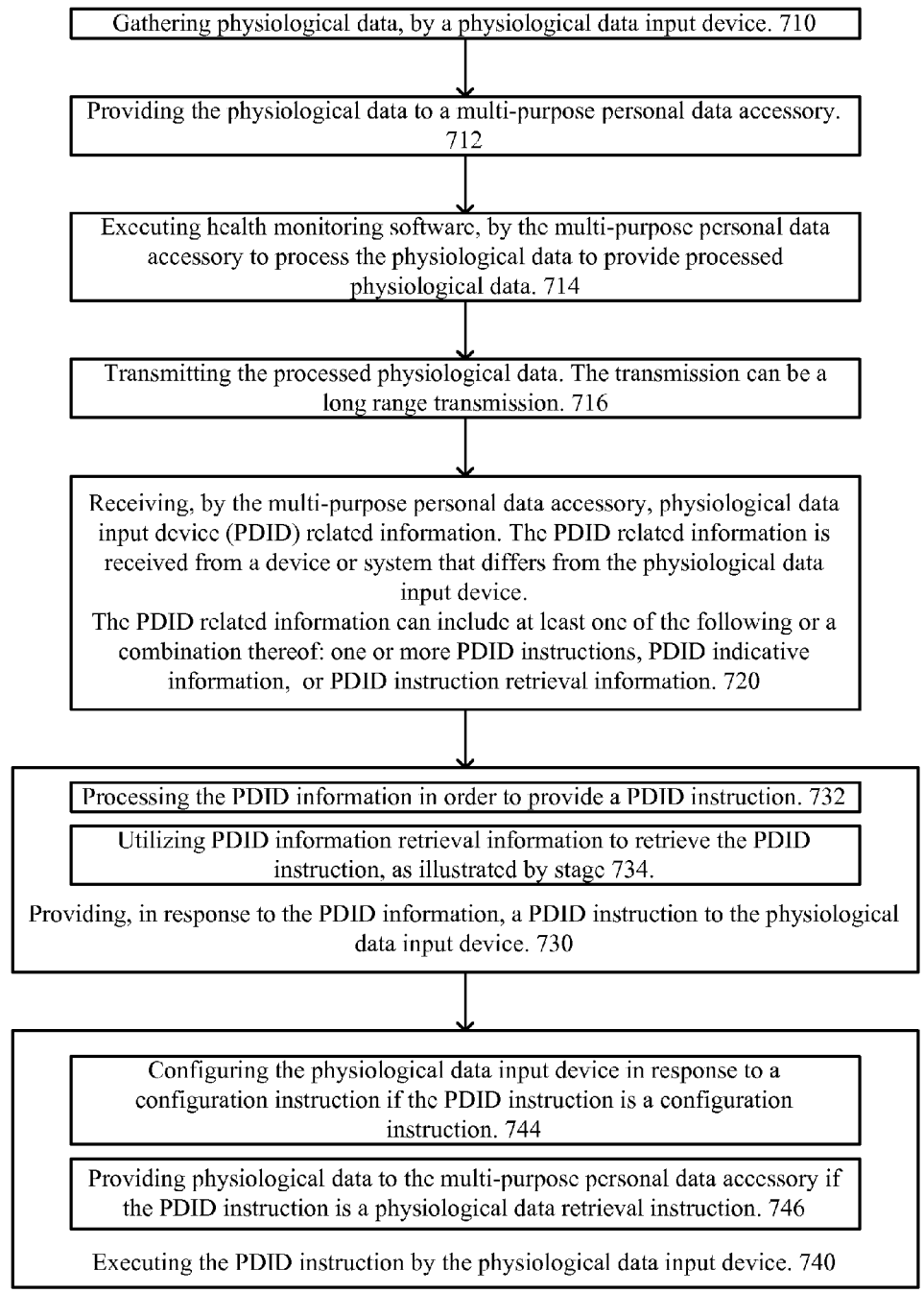
FIG. 14 illustrates a flow chart of a method for health monitoring according to a further embodiment of the invention.

FIG. 14 illustrates a flow chart of method 700 for health monitoring according to another embodiment of the invention.

Method 700 starts by stage 710 of gathering physiological data, by a physiological data input device.

Stage 710 is followed by stage 712 of providing the physiological data to a multi-purpose personal data accessory.

Stage 712 is followed by stage 714 of executing health monitoring software, by the multi-purpose personal data accessory to process the physiological data to provide processed physiological data.

Stage 714 is followed by stage 716 of transmitting the processed physiological data. The transmission can be a long range transmission.

Method 700 also includes stages 720 and 730. Each of these stages can be executed in parallel to stages 710, 712, 714 and 716 but this is not necessarily so.

Stage 720 includes receiving, by the multi-purpose personal data accessory, physiological data input device (PDID) related information. The PDID related information is received from a device or system that differs from the physiological data input device.

The PDID related information can include at least one of the following or a combination thereof: (i) one or more PDID instructions, (ii) PDID indicative information—information than can be indicative of one or more PDID related instructions (for example—can be a code that is representative of such an instruction), (iii) PDID instruction retrieval information—information that assists in retrieving one or more PDID related instructions (for example—a link or other type of retrieval information that can assist in a retrieval of one or more instruction), and the like.

It is noted that the PDID related information can be received by using a communication link that is used to exchange various types of information. This communication link can be used for receiving information related to applications or services that are not related to the health monitoring. For example, the multi-purpose personal data accessory can be mobile phone capable of receiving various types of information including vocal information, MMS messages, video streams, and SMS messages.

Accordingly, stage 720 can include detecting, by the multi-purpose personal data accessory, that it received PDID related information. The detection can include parsing an SMS message, searching for a predefined string or content, and the like.

Stage 720 is followed by stage 730 of providing, in response to the PDID information, a PDID instruction to the physiological data input device. It is noted that if the PDID related information is a PDID instruction than it can be provided "as is" (or with only insignificant processing) to the physiological data input device. Insignificant processing can include format conversion—from multi-purpose personal data accessory to PDID compliant format.

According to another embodiment of the invention stage 730 includes processing the PDID information in order to provide a PDID instruction, as illustrated by stage 732. The processing can include, for example, encoding the PDID information, or using said PDID information to select a PDID instruction.

According to another embodiment of the invention PDID information retrieval information is used to retrieve the PDID instruction, as illustrated by stage 734.

Conveniently, stage 734 includes: (i) accessing a remote entity; (ii) retrieving a PDID instruction from the remote entity; and (iii) sending the PDID instruction to the physiological data input device. Stage 734 can include accessing a remote entity that provides web based services; providing the remote entity an identifier included within the PDID related information; and retrieving from the remote entity a PDID instruction.

Stage 730 is followed by stage 740 of executing the PDID instruction by the physiological data input device.

Stage 740 can include at least one of the following or a combination thereof: (i) providing (742) configuration information to the multi-purpose personal data accessory; (ii) configuring (744) the physiological data input device in response to a configuration instruction if the PDID instruction is a configuration instruction; (iii) providing (746) physiological data to the multi-purpose personal data accessory if the PDID instruction is a physiological data retrieval instruction.

It will be appreciated by persons skilled in the art that the present invention is not limited to what has been particularly shown and described hereinabove.

Those skilled in the art will readily appreciate that various modifications and changes may be applied to the preferred embodiments of the invention as hereinbefore exemplified without departing from its scope as defined in and by the appended claims.

We claim:

1. A personal health monitor comprising: a physiological data input device operative to gather physiological data; and a multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity; wherein the physiological data input device controls a transmission of the physiological data to the multi-purpose personal data accessory; wherein the physiological data input device comprises a receiver that is maintained in a low power mode during idle periods that are determined by the physiological data input device.

2. The personal health monitor of claim 1 wherein the physiological data input device determines whether physiological data can be sent from the physiological data input device to the multi-purpose personal data accessory.

3. The personal health monitor of claim 2 wherein the physiological data input device generates an alert in response to a determination that a transmission of physiological data to the multi-purpose personal data accessory is expected to fail.

4. A personal health monitor comprising: a physiological data input device operative to gather physiological data and a multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity; wherein the multi-purpose personal data accessory is adapted to receive physiological data input device related information and to provide, in response to the physiological data input device related information, a physiological data input device instruction to the physiological data input device; wherein the physiological data input device is adapted to send configuration information to the multi-purpose personal data accessory in response to the physiological data input device instruction.

5. A personal health monitor comprising: a physiological data input device operative to gather physiological data; and a multi-purpose personal data accessory, whereas the multi-purpose personal data accessory is adapted to execute health monitoring software such as to enable the multi-purpose personal data accessory to receive the physiological data, process the physiological data to provide processed physiological data and control a long range transmission of the processed physiological data to a remote entity; wherein the multi-purpose personal data accessory is adapted to receive physiological data input device related information and to provide, in response to the physiological data input device related information, a physiological data input device instruction to the physiological data input device; wherein the physiological data input device instruction comprises a configuration instruction and wherein the physiological data input device is adapted to configure itself in response to configuration instruction.

6. The personal health monitor according to claim 5 wherein the physiological data input device instruction is a physiological data retrieval instruction and wherein the physiological data input device is adapted to send physiological data in response to the physiological data retrieval instructions.

7. The personal health monitor according to claim 5 wherein the multi-purpose personal data accessory is adapted to extract the physiological data input device instruction from the physiological data input device related information.

8. The personal health monitor according to claim 5 wherein the multi-purpose personal data accessory is adapted to access a remote entity; retrieve a physiological data input device instruction from the remote entity; and send the physiological data input device instruction to the physiological data input device.

9. The personal health monitor according to claim 8 wherein the multi-purpose personal data accessory is adapted access a remote entity that provides web based services; provide to the remote entity an identifier included within the physiological data input device related information; and retrieve from the remote entity physiological data input device instructions.

10. The personal health monitor according to claim 9 wherein the multi-purpose personal data accessory is adapted send a physiological data input device instruction that is selected from a list consisting of physiological data retrieval instructions and configuration instructions.

11. A method for health monitoring, comprising: gathering physiological data, by a physiological data input device; providing the physiological data to a multi-purpose personal data accessory using a communication link that is controlled by the physiological data input device; executing health monitoring software, by the multi-purpose personal data accessory to process the physiological data to provide processed physiological data; transmitting the processed physiological data and maintaining a receiver of the physiological data input device in a low power mode during idle periods that are determined by the physiological data input device.

12. The method according to claim 11 comprising determining by the physiological data input device whether physiological data can be sent from the physiological data input device to the multi-purpose personal data accessory.

13. The method according to claim 11 comprising generating an alert, by the physiological data input device, in response to a determination that a transmission of physiological data to the multi-purpose personal data accessory is expected to fail.

14. A method for health monitoring, comprising: gathering physiological data, by a physiological data input device; providing the physiological data to a multi-purpose personal data accessory; executing health monitoring software, by the multi-purpose personal data accessory to process the physiological data to provide processed physiological data; transmitting the processed physiological data; receiving physiological data input device related information by the multi-purpose personal data accessory; and providing, in response to the physiological data input device related information, a physiological data input device instruction to the physiological data input device; the method further comprising sending configuration information, by the physiological data input device, to the multi-purpose personal data accessory in response to the physiological data input device instruction wherein the physiological data input device instruction comprises a configuration instruction and wherein the method comprises configuring the physiological data input device in response to the configuration instruction.

15. The method according to claim 14 wherein the physiological data input device related information comprises a physiological data retrieval instruction and wherein the method comprises sending physiological data from the physiological data input device in response to the physiological data retrieval instruction.

16. The method according to claim 14 comprising extracting the physiological data input device instruction by the multi-purpose personal data accessory.

17. The method according to claim 14 comprising accessing a remote entity; retrieving a physiological data input device instruction from the remote entity; and sending the physiological data input device instruction to the physiological data input device.

18. The method according to claim 14 comprising accessing a remote entity that provides web based services; providing to the remote entity an identifier included within the physiological data input device related information; and retrieving from the remote entity physiological data input device instructions.

19. The method according to claim 14 comprising sending, by the multi-purpose personal data accessory, a physiological data input device instruction that is selected from a list consisting of physiological data retrieval instructions and configuration instructions.

* * * * *